US006670456B2

(12) United States Patent
Frank et al.

(10) Patent No.: US 6,670,456 B2
(45) Date of Patent: Dec. 30, 2003

(54) ACTINIUM-225 COMPLEXES AND CONJUGATES FOR TARGETED RADIOTHERAPY

(75) Inventors: R. Keith Frank, Lake Jackson, TX (US); Garry E. Kiefer, Lake Jackson, TX (US); Jaime Simon, Angleton, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/085,930

(22) Filed: Feb. 27, 2002

(65) Prior Publication Data

US 2003/0023050 A1 Jan. 30, 2003

Related U.S. Application Data

(60) Provisional application No. 60/272,288, filed on Feb. 28, 2001.

(51) Int. Cl.$^7$ .................................................. C07F 5/00
(52) U.S. Cl. ...................... 534/11; 424/1.11; 424/1.65; 424/9.1; 514/156; 514/183; 514/188; 514/241; 514/247
(58) Field of Search ........................ 534/11–13; 424/9.1, 424/1.11, 1.65, 1.69; 514/156, 183, 188, 241, 247

(56) References Cited

U.S. PATENT DOCUMENTS

| | | | |
|---|---|---|---|
| 4,897,254 A | 1/1990 | Simon et al. ................. 424/1.1 |
| 5,342,925 A | 8/1994 | Wilson et al. ................. 534/10 |
| 5,428,139 A | 6/1995 | Kiefer et al. ................. 534/10 |
| 5,435,990 A | 7/1995 | Cheng et al. ............... 424/153 |
| 5,480,990 A | 1/1996 | Kiefer et al. ................ 540/465 |
| 5,652,361 A | 7/1997 | Simon et al. ................ 540/474 |
| 5,696,239 A | 12/1997 | Wilson et al. ................. 534/10 |
| 5,739,294 A | 4/1998 | Kiefer et al. ................. 534/15 |
| 5,750,660 A | * 5/1998 | Kiefer et al. ................. 534/10 |
| 5,756,065 A | 5/1998 | Wilson et al. ............. 424/1.53 |
| 5,834,456 A | * 11/1998 | Kiefer et al. ................. 514/86 |

FOREIGN PATENT DOCUMENTS

| | | | |
|---|---|---|---|
| WO | WO 99/30745 | 6/1999 | .......... A61K/51/00 |
| WO | WO 00/59896 | 10/2000 | .......... C07D/259/00 |
| WO | WO 01/66155 | 9/2001 | .......... A61K/51/04 |
| WO | WO 02/05859 | 1/2002 | .......... A61K/51/04 |
| WO | WO 02/22000 | 3/2002 | |

OTHER PUBLICATIONS

"Cytotoxicity of $^{213}$Bi– and $^{225}$Ac–Immunoconjugates," *Nuclear Medicine Communications*, vol. 16, 1995, pp. 468–476, Kaspersen et al.

"Bismuth–212–Labeled Anti–Tac Monoclonal Antibody: Alpha–Particle–Emitting Radionuclides as Modalities for Radioimmunotherapy," *Proc. Natl. Acad. Sci. USA*, vol. 83, Jan. 1986, pp. 474–478. Kozak et al.

"Radioimmunotherapy With Alpha–Particle–Emitting Immunoconjugates," *Science*, vol. 240, 1988, pp. 1024–1026. Macklis et al.

"The Feasibility of $^{225}$Ac as a Source of Alpha–Particles in Radioimmunotherapy," *Nuclear Medicine Communications*, vol. 14, 1993, pp. 121–125. Geerlings et al.

G. J. Beyer, et al., "Comparison of the Biodistribution of $^{225}$Ac and Radio–Lanthanides as Citrate Complexes," *Isotoperpraxis*, vol. 26, 1990, pp. 111–114.

"The Influence of EDTMP–Concentration on the Biodistribution of Radio–Lanthanides and 225–Ac in Tumor–Bearing Mice," *Nuclear Medicine & Biology*, vol. 24, 1997, pp. 367–372. Beyer et al.

K. A. Deal, et al., "Improved in Vivo Stability of Actinium–225– Macrocyclic Complexes," *J. Med. Chem.*, vol. 42, 1999, pp. 298–292.

G. Kohler, et al., "Continuous Cultures of Fused Cells Secreting Antibody of Predefined Specificity," *Nature*, vol. 256, Aug. 1975, pp. 495–497.

G. Kohler, et al., "Derivation of Specific Antibody–Producing Tissue Culture and Tumor Lines By Cell Fusion," *Eur. J. Immunol.*, vol. 6, 1976, pp. 511–519.

"Conjugation of Antibodies with Bifunctional Chelating Agents: Isothiocyanate and Bromoacetamide Reagents, Methods of Analysis, and Subsequent Addition of Metal Ions." *Analytical Biochemistry*, vol. 142, 1984, pp. 68–74. Meares et al.

G. E. Krejcarek and K. L. Tucker, "Covalent Attachment of Chelating Groups to Macromolecules," *Biochemical and Biophysical Research Communications*, vol. 77, No. 2, 1997, pp. 581–585.

J. K. Moran, et al., "Improved Synthesis of 6–[p–(Bromoacetamide)benzyl]–1,4,8,11–tetraazacyclotetradecane–N, N', N", N'''–tetraacetic Acid and Development of a Thin–Layer Assay for Thiol–Reactive Bifunctional Chelating Agents," *Bioconjugate Chem.*, vol. 6, No. 3, 1995, pp. 296–301.

C. F. Meares and O. Renn, "Large–Scale Synthesis of the Bifunctional Chelating Agent 2–(p–Nitrobenzyl)–1,4,7,10–tetraazacyclododecane–N,N',N",N '''–tetraacetic Acid, and the Determination of Its Enantiomeric Purity by Chiral Chromatography," *Bioconjugate Chem.*, vol. 3, No. 6, 1992 pp. 563–569.

* cited by examiner

*Primary Examiner*—Dameron L. Jones

(57) ABSTRACT

Actinium-225 complexes comprising functionalized polyazamacrocyclic chelant compounds are disclosed. Such complexes show improved stability and can be conjugated to a biological carrier.

10 Claims, No Drawings

ACTINIUM-225 COMPLEXES AND CONJUGATES FOR TARGETED RADIOTHERAPY

This application claims the benefit of U.S. Provisional Application No. 60/272,288 filed Feb. 28, 2001.

This invention relates to actinium-225 ($^{225}$Ac) complexes with fuctionalized chelants, their conjugates and their use for targeted radiotherapy.

The use of radionuclides complexed with suitable chelants, as well as their conjugates (that is, such complexes covalently attached to a biologically active carrier, e.g., protein) for diagnosis of cancer and/or therapeutic treatment of cancer in mammals is known. These biochemically engineered molecules provide the tumor specificity and the radioisotope provides potent cytotoxicity. See, for example, U.S. Pat. Nos. 4,897,254; 5,342,925; 5,435,990; 5,652,361; 5,696,239; and 5,756,065.

It has been recognized that antibody-targeted alpha particles would allow extraordinarily potent, single cell-specific killing with minimal toxicity to normal cells or the patient. The use of alpha particles as an alternative to more traditional classes of radiation is derived from the particle's kinetic characteristics and the radioactive half-life of their source isotope, as well as from the properties of the target-selective carrier moiety for the source isotope. The use of alpha-emitting radionuclides is highly desirable for the following reasons: (a) a single atom can kill a cell making them hundreds to thousands of times more potent than even the most potent toxins or drugs; (b) the range of alpha particles is only about 50 microns, so that adjacent tissues are not harmed; (c) the chelated atoms on fully human or humanized antibodies are unlikely to be immunogenic and can be repeatedly dosed; (d) the radioactive atoms decay to harmless stable atoms; (e) killing can occur from inside or outside of the cell; (f) killing is by apoptosis and by double stranded DNA breaks and repair is not likely.

Specific cytotoxic effects of "alpha particle-emitting radioimmunoconjugates" have been demonstrated in several experimental systems. Specific in vitro cell-killing has been demonstrated against a human epidermoid cell line using $^{213}$Bi- and $^{225}$Ac-containing immunoconjugates, see, for example, Kaspersen et al, Nuclear Medicine Communications, Vol. 15, pp. 468–476 (1995). Efficient and specific cell kill by the $^{212}$Bi-labeled anti-Tac (CD25) monoclonal antibody has been demonstrated against an adult T-cell leukemia cell line in vitro, see, for example, R. W. Kozak et al, Proc. Natl. Acad. Sci. USA, Vol. 83, pp. 474–478 (1986). In other experiments, mice inoculated intraperitoneally with the murine tumor line EL-4 were cured of their ascites after intraperitoneal injection of 150 μCi of a $^{212}$Bi-labeled antibody conjugate, see, for example, R. M. Macklis et al, Science, Vol. 240, pp. 1024–1026 (1988).

Potential for use of $^{225}$Ac in radiotherapy of cancer has also been recognized due to its favorable properties. This isotope decays with a radioactive half-life of 10 days into a cascade of short lived alpha- and beta-emitting isotopes. See, for example, M. W. Geerlings et al, Nuclear Medicine Communications, Vol. 14, pp. 121–125 (1993) and Kaspersen et al, Nuclear Medicine Communications, Vol. 15, pp. 468–476 (1995). However, the use of $^{225}$Ac in radioimmunotherapy has been hampered due to its toxicity and lack of a suitable carrier which will deliver it to the targeted cells.

In an effort to reduce the toxicity of $^{225}$Ac, numerous chelating agents such as, for example, 1,4,7,10-tetraazacyclododecane-1,4,7,10-tetraacetic acid (DOTA), diethylenetriaminepentaacetic acid (DTPA), ethylenediaminetetracetic acid (EDTA), 1,4,7,10,13-pentaazacyclopentadecane-1,4,7,10,13-pentaacetic acid (PEPA), and 1,4,7,10,13,16-hexaazacyclohexadecane-1,4,7,10,13,16-hexaacetic acid (HEHA) have been complexed with $^{225}$Ac and evaluated in vivo for toxicity and stability. However, the toxicity of these complexes has proved to be still substantial.

G. J. Beyer et al, Isotoperpraxis, Vol. 26, pp. 111–114 (1990), has evaluated the in vivo uptake of $^{225}$Ac-citrate and compared it to $^{169}$Yb-citrate. This study has found that $^{225}$Ac-citrate had more efficient blood clearance, greater liver uptake, and lower bone uptake than $^{169}$Yb-citrate.

G. J. Beyer et al, Nucl. Med. & Biol., Vol. 24, pp. 367–372 (1997), has evaluated EDTMP (ethylenediaminetetramethylenephosphonic acid) as a chelant for $^{225}$Ac. The study has found that EDTMP, depending on its concentration, reduces the liver uptake. However, the liver uptake of $^{225}$Ac-EDTMP is still substantial and excretion of $^{225}$Ac-EDTMP is poor. The study has also suggested that greater efficacy in endoradionuclide therapy of bone metastasis can be expected with the use of $^{225}$Ac-EDTMP due to the alpha-radiation.

K. A. Deal et al, J. Med. Chem., Vol 42, pp. 298–2992 (1999), has evaluated biodistribution of a number of $^{225}$Ac chelates. It has been observed that the structure of the chelant has a dramatic effect on the biodistribution of $^{225}$Ac. HEHA (1,4,7,10,13,16-hexaazacyclohexadecane-1,4,7,10,13,16-hexaacetic acid) was the largest macrocyclic chelant. $^{225}$Ac readily formed a complex with HEHA. Exceptional in vivo stability and reduced toxicity has been observed for $^{225}$Ac-HEHA. This has been attributed to the large size and macrocyclic effect of HEHA.

Although various chelating agents were suggested and evaluated as carriers for $^{225}$Ac, up to now $^{225}$Ac has not been successfully chelated to an antibody and no successful therapeutic use of $^{225}$Ac in animals or humans has been reported, presumably due to its inherent toxicity and/or stability problems of its complexes.

It would be desirable to provide complexes comprising $^{225}$Ac and functionalized chelants which are kinetically and thermodynamically inert for use in therapeutic applications.

It would also be desirable to provide conjugates of such $^{225}$Ac complexes with a biological carrier. The biological carrier in these conjugates would provide the tumor specificity and the $^{225}$Ac isotope would provide potent cytotoxicity.

Another desirable property of these conjugates includes physiological compatibility which would permit the $^{225}$Ac complex, if separated from its targeting, conjugated biological carrier in vivo, to be soluble in physiological fluids and thus be rapidly eliminated from the body.

The present invention is directed to $^{225}$Ac complexes and their conjugates with a biological carrier. The $^{225}$Ac complexes and conjugates of the present invention are useful for the treatment of cancer in mammals, especially humans.

More specifically, the present invention is directed to $^{225}$Ac complexes comprising a functionalized polyazamacrocyclic chelant compound of the formula I hereinbelow:

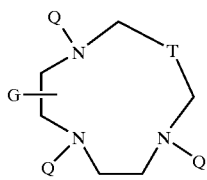

wherein:

T is 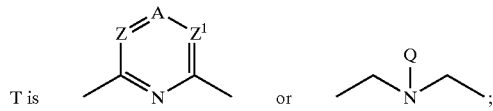

G is independently hydrogen or

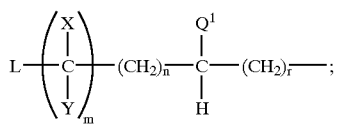

each Q is independently hydrogen, $(CHR^5)_pCO_2R$ or $(CHR^5)_pPO_3R^6R^7$ or

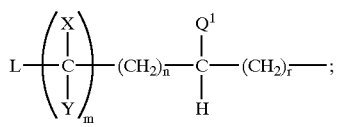

$Q^1$ is hydrogen, $(CHR^5)_wCO_2R$ or $(CHR^5)_wPO_3R^6R^7$;
each R is independently hydrogen, benzyl or $C_1$–$C_4$ alkyl;
$R^6$ and $R^7$ are independently H, $C_1$–$C_6$ alkyl or ($C_1$–$C_2$ alkyl)phenyl;
each $R^5$ is independently hydrogen; $C_1$–$C_4$ alkyl or ($C_1$–$C_2$ alkyl)phenyl;
with the proviso that at least two of the sum of Q and $Q^1$ must be other than hydrogen;
A is CH, N, C—Br, C—Cl, C—$SO_3H$, C—$OR^8$, C—$OR^9N^+$—$R^{10}X^-$, or

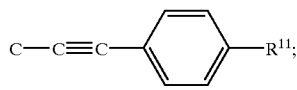

Z and $Z^1$ independently are CH, N, C—$SO_3H$, $N^+$—$R^{10}X^-$, C—$CH_2$—$OR^8$ or C—C(O)—$R^{11}$;
$R^8$ is H, $C_1$–$C_5$ alkyl, benzyl, or benzyl substituted with at least one $R^{12}$;
$R^9$ is $C_1$–$C_{16}$ alkylamino;
$R^{10}$ is $C_1$–$C_{16}$ alkyl, benzyl, or benzyl substituted with at least one $R^{12}$;
$R^{11}$ is —O—($C_1$–$C_3$ alkyl), OH or $NHR^{13}$;
$R^{12}$ is H, $NO_2$, $NH_2$, isothiocyanato, semicarbazido, thiosemicarbazido, maleimido, bromoacetamido or carboxyl;
$R^{13}$ is $C_1$–$C_5$ alkyl;
X and Y are each independently hydrogen or may be taken with an adjacent X and Y to form an additional carbon—carbon bond;
n is 0 or 1;

m is an integer from 0 to 10 inclusive;
p is 1 or 2;
r is 0 or 1;
w is 0 or 1;
with the proviso that n is only 1 when X and/or Y form an additional carbon—carbon bond, and the sum of r and w is 0 or 1;
L is a linker/spacer group covalently bonded to, and replaces one hydrogen atom of one of the carbon atoms to which it is joined, said linker/spacer group being represented by the formula

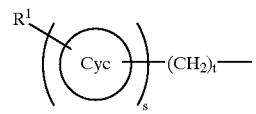

wherein:
s is an integer of 0 or 1;
t is an integer of 0 to 20 inclusive;
$R^1$ is H or an electrophilic or nucleophilic moiety which allows for covalent attachment to a biological carrier, or synthetic linker which can be attached to a biological carrier, or precursor thereof; and
Cyc represents a cyclic aliphatic moiety, aromatic moiety, aliphatic heterocyclic moiety, or aromatic heterocyclic moiety, each of said moieties optionally substituted with one or more groups which do not interfere with binding to a biological carrier;
with the proviso that when $R^1$ is H, the linkage to the biological carrier is through one of Q or $Q^1$; and with the proviso that when $R^1$ is other than H, at least one of Q and $Q^1$ must be $(CHR^5)_pPO_3R^6R^7$; and with further proviso that when Q is $(CHR^5)_pCO_2R$, $Q^1$ is $(CHR^5)_wCO_2R$, R is H, $R^5$ is H, and $R^1$ is H, then the sum of m, n, p, r, s, t, and w is greater than 1;

or a pharmaceutically acceptable salts thereof; complexed with $^{225}Ac$.

Even more specifically, the present invention is directed to $^{225}Ac$ complexes comprising a functionalized polyazamacrocyclic chelant compound of the formula II, III, IV or V hereinbelow:

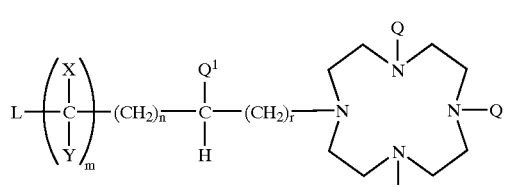

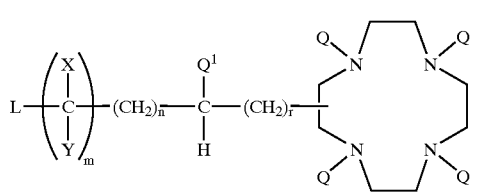

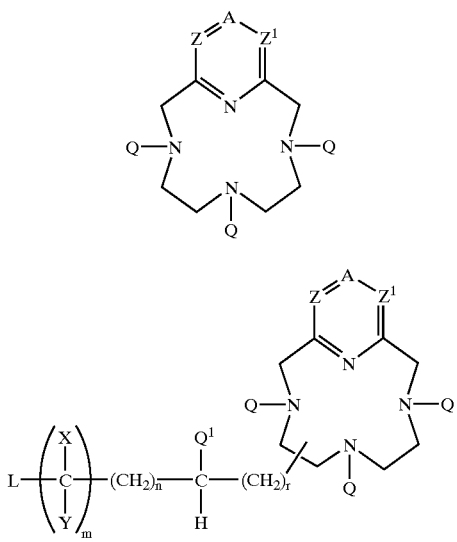

wherein the substituents are as defined above.

The present invention is also directed to a conjugate comprising the aforementioned $^{225}$Ac complex covalently attached to a biological carrier.

The present invention is also directed to a conjugate comprising the $^{225}$Ac complex of DOTA (1,4,7,10-tetraazacyclododecane-1,4,7,10-tetraacetic acid) covalently attached via amide linkage to a biological carrier.

The present invention also includes formulations comprising the conjugates of this invention and a pharmaceutically acceptable carrier, especially formulations where the pharmaceutically acceptable carrier is a liquid.

The present invention is also directed to a method of therapeutic treatment of a mammal having cancer which comprises administering to said mammal a therapeutically effective amount of the formulation of this invention.

Surprisingly, the $^{225}$Ac complexes and conjugates of this invention are relatively stable (that is, do not easily dissociate) and some display rapid clearance from the whole body and some non-target organs, such as liver and kidney. Additionally, the alpha particle-emitting $^{225}$Ac complexes and conjugates of this invention are expected to have several advantages over beta particle-emitting cytotoxic agents including higher energy and more potent emissions, less hazardous waste, expected lower effective dose, the potential for outpatient treatment, better retention at the target sites, and higher target to non-target radiation ratios.

As used herein, the term "$^{225}$Ac complex" refers to a polyazamacrocyclic functionalized chelant compound of formula I complexed with $^{225}$Ac radionuclide.

As used herein, the term "$^{225}$Ac conjugate" refers to $^{225}$Ac complex of the present invention that is covalently attached to a biological carrier.

As used herein, the term "mammal" means animals that nourish their young with milk secreted by mammary glands, preferably humans.

As used herein, the term "biological carrier" refers to any protein, antibody, antibody fragment, hormone, peptide, growth factor, antigen, hapten or any other carrier which functions in this invention to recognize a specific biological target site. Antibody and antibody fragment refers to any polyclonal, monoclonal, chimeric, human, mammalian, single chains, dimeric and tetrameric antibody or antibody fragment. Such biological carrier, when attached to a functionalized complex, serves to carry the attached $^{225}$Ac ion to specific targeted tissues. The term "antibody" refers to any polyclonal, monoclonal, chimeric antibody or heteroantibody. Preferably the antibodies used in the $^{225}$Ac conjugates of the present invention are monoclonal antibodies having high specificity for the desired cancer cells. Antibodies used in the present invention may be directed against, for example, cancer, tumors, leukemias, autoimune disorders involving cells of the immune system, normal cells that need to be ablated such as bone marrow and prostate tissue, virus infected cells including HIV, mycoplasma, differentiation and other cell membrane antigens, patogen surface antigens and any biologically active molecules. Some examples of antibodies are HuM195 (anti-CD33), CC-11, CC-46,CC-49, CC-49 F(ab')$_2$, CC-83, CC-83 F(ab')$_2$, and B72.3. Particularly preferred antibody for use in the practice of the present invention is HuM195. Antibody fragment includes Fab fragments and F(ab')$_2$ fragments, and any portion of an antibody having specificity toward a desired epitope or epitopes. The antibodies which may be used in the $^{225}$Ac conjugates of the present invention can be prepared by techniques well known in the art. Highly specific monoclonal antibodies can be produced by hybridization techniques well known in the art, see, for example, Kohler and Milstein, Nature, 256, 495–497 (1975); and Eur. J. Immunol., 511–519 (1976).

As used herein, "pharmaceutically acceptable salt" means any salt of a compound of formula I which is sufficiently non-toxic to be useful in therapy of mammals. Representative of those salts, which are formed by standard reactions, from both organic and inorganic sources include, for example, sulfuric, hydrochloric, phosphoric, acetic, succinic, citric, lactic, maleic, fumaric, palmitic, cholic, palmoic, mucic, glutamic, d-camphoric, glutaric, glycolic, phthalic, tartaric, formic, lauric, steric, salicylic, methanesulfonic, bensenesulfonic, sorbic, picric, benzoic, cinnamic and other suitable acids. Also included are salts formed by standard reactions from both organic and inorganic sources such as ammonium, alkali metal ions, alkaline earth metal ions, and other similar ions. Preferred are the salts of the compounds of formula I where the salt is potassium, sodium, ammonium, or mixtures thereof.

As used herein, the term "therapeutically effective amount" means an amount of the $^{225}$Ac conjugate that produces a therapeutic effect on the disease treated. The therapeutically effective amount will vary depending on the mammal, the $^{225}$Ac conjugate and the method of its administration (for example, oral or parenteral). A person of ordinary skill in the art can determine the therapeutically effective amount of the $^{225}$Ac conjugate.

In the practice of the present invention the $^{225}$Ac conjugate may be administered per se or as a component of a pharmaceutically acceptable formulation.

Thus, the present invention may be practiced with the $^{225}$Ac conjugate being provided in pharmaceutical formulation, both for veterinary and for human medical use. Such pharmaceutical formulations comprise the active agent (the $^{225}$Ac conjugate) together with a physiologically acceptable carrier, excipient or vehicle therefore. The carrier (s) must be physiologically acceptable in the sense of being compatible with the other ingredient(s) in the formulation and not unsuitably deleterious to the recipient thereof. The $^{225}$Ac conjugate is provided in a therapeutically effective amount, as described above, and in a quantity appropriate to achieve the desired dose.

The formulations include those suitable for parenteral (including subcutaneous, intramuscular, intraperitoneal, and intravenous), oral, rectal, topical, nasal, or ophthalmic administration. Formulations may be prepared by any methods well known in the art of pharmacy. Such methods include the step of bringing the $^{225}$Ac conjugate into association with a carrier, excipient or vehicle therefore. In general, the formulation may be prepared by uniformly and intimately bringing the $^{225}$Ac conjugate into association with a liquid carrier, a finely divided solid carrier, or both, and then, if necessary, shaping the product into desired formulation. In addition, the formulations of this invention may further include one or more accessory ingredient(s) selected from diluents, buffers, binders, disintegrants, surface active agents, thickeners, lubricants, preservatives, and the like. In addition, a treatment regime might include pretreatment with non-radioactive carrier.

Injectable formulations of the present invention may be either in suspensions or solution form. In the preparation of suitable formulations it will be recognized that, in general, the water solubility of the salt is greater than the acid form. In solution form the complex (or when desired the separate components) is dissolved in a physiologically acceptable carrier. Such carriers comprise a suitable solvent, preservatives such as free radical quenching agents, for example, ascorbic acid, benzyl alcohol or any other suitable molecule, if needed, and buffers. Useful solvents include, for example, water, aqueous alcohols, glycols, and phosphonate or carbonate esters. Such aqueous solutions contain no more than 50 percent of the organic solvent by volume.

Injectable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, polyols, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethyleneoxide adducts, naphthalenesulfonates, alkylbenzenesulfonates, and polyoxyethylene sorbitane esters.

In the context of the present invention the terms "functionalized chelant" and "bifunctional chelant" are used interchangeably and refer to compounds which have the dual functionality of sequestering metal ions plus the ability to covalently bind a biological carrier having specificity for tumor cell epitopes or antigens. Such compounds are of great utility for therapeutic and diagnostic applications when they are, for example, complexed with radioactive metal ions and covalently attached to a specific antibody. These types of complexes have been used to carry radioactive metals to tumor cells which are targeted by the specificity of the attached antibody [see, for example, Mears et al., Anal. Biochem. 142, 68–74 (1984); Krejcarek et al., Biochem. And Biophys. Res. Comm. 77, 581–585 (1977)].

The polyazamacrocyclic functionalized chelant compounds of formulas II, III, IV and V useful in the practice of the present invention are known in the art. See, for example, U.S. Pat. Nos. 5,435,990; 5,652,361; 5,428,139; 5,480,990; and 5,739,294.

The polyazamacrocyclic functionalized chelants of formula I useful in the practice of the present invention can be prepared by known methods. General synthetic approach to a twelve-membered macrocyclic, bifunctional chelant of the present invention as represented by formula II involves monofuctionalization of a free-base macrocycle (for example, 1,4,7,10-tetraazacyclododecane) at only one of the nitrogen atoms with an appropriate electrophile (for example, any appropriately substituted alpha-halocarboxylic acid ester). This electrophile must possess a suitable linker moiety which would allow covalent attachment of bifunctional ligand to a biological carrier. Various synthetic routes to functionalized chelants of formula II have been described in U.S. Pat. Nos. 5,435,990; 5,652,361, both incorporated herein by reference.

General synthetic approach to a twelve-membered macrocyclic, bifunctional chelant of the present invention as represented by formula III is more complex and involves synthesis of a backbone-functionalized macrocycle. Various synthetic routes to functionalized chelants of formula III have been described in J. K. Moran, et al, Bioconjugate Chem., 6(3), 296–301 (1995); O. Renn, et al, Bioconjugate Chem., 3(6), 563–9 (1992).

General synthetic approach to a macrocyclic, bifunctional chelant of the present invention as represented by formula IV involves functionalization of the base macrocycle (for example, 3,6,9,15-tetraazabicyclo[9.3.1]-pentadeca-1(15), 11,13-triene) with chelating and/or linking functionalities. Various synthetic routes to functionalized chelants of formula IV have been described in U.S. Pat. Nos. 5,428,139; 5,480,990; and 5,739,294.

General synthetic approach to a twelve-membered macrocyclic, bifunctional chelant of the present invention as represented by formula V involves the use of functionalized moieties in the formation of the twelve-membered tetraazamacrocycle in order to accomplish backbone substitution. Various synthetic routes to functionalized chelants of formula V can be envisioned by substituting these moieties into the schemes presented in U.S. Pat. Nos. 5,428,139; 5,480,990; and 5,739,294.

The method of obtaining $^{225}$Ac radionuclide is not critical to the present invention. For example, $^{225}$Ac can be prepared in a cyclotron. $^{225}$Ac can be obtained in pure form from Department of Energy (DOE), U.S.A., and Institute for Transuranium Elements (ITU), Karlsruhe, Germany.

When forming the $^{225}$Ac complexes of the present invention, the degree of complexation is advantageously high. As used herein, the terms "degree of complexation" and "percent complexation" are used interchangeably and are defined to mean the percentage of the $^{225}$Ac that is successfully complexed with the bifunctional chelant divided by the total $^{225}$Ac used in the complexation reaction. Preferably, the percent complexation when making the $^{225}$Ac complexes of the present reaction is greater than 50%, more preferably greater than 70%, even more preferably greater than 90% and yet even more preferably greater than 95%, as measured by cation exchange chromatography within 24 hours after complexation.

The $^{225}$Ac conjugates of the present invention can be prepared by first forming the complex and then attaching to the biological carrier. Thus, the process involves preparing or obtaining the ligand, forming the complex with $^{225}$Ac and then adding the biological carrier. Alternatively, the process may involve first conjugation of the ligand to the biological carrier and then the formation of the complex with $^{225}$Ac. Any suitable process that results in the formation of the $^{225}$Ac conjugates of this invention is within the scope of the present invention.

EXAMPLES

Materials

All materials were from common commercial sources unless stated otherwise.

EDTA is ethylenediaminetetraacetic acid.

Sephadex C-25 resin is a cation exchange resin, sold by Pharmacia Inc.

$^{225}$Ac was received from Oak Ridge National Laboratory, Oak Ridge, Tenn., as a solid nitrate salt. It was dissolved in 0.1 M nitric acid and diluted further.

TMAA (tetramethyl ammonium acetate) is from Lancaster, Windham, N.H.

The following examples are provided to further illustrate the present invention, and should not be construed as limiting thereof.

Examples 1–5

Preparation of $^{225}$Ac-Chelant Complexes

Table 1 lists the chelants that were used to form the complexes in Examples 1–5. Methods known in the art can be employed to convert these chelants into bifunctional molecules capable of forming conjugates. For example, the nitro group in chelant 1 can be reduced to an amine and subsequently converted to an isothiocyanate; a bifunctional analog of chelant 4 can be prepared by attaching a linking group to one of the acetate carbons.

TABLE 1

Chelants used for complexation.

| Chelant | Name |
|---|---|
| 1 | 1-(α-(2-methoxy-5-nitrophenyl)-acetic acid-4,7,10-methylene-phosphonic acid trimethyl ester-1,4,7,10-tetraazacyclododecane |
| 2 | 3,6,9,15-tetraazabicyclo-[9.3.1]pentadeca-1(15),11,13-triene-3,6,9-methylenephosphonic acid |
| 3 | 3,6,9,15-tetraazabicyclo-[9.3.1]pentadeca-1(15),11,13-triene-3,6,9-methylenphosphonic acid tributyl ester |
| 4 | 3,6,9,15-tetraazabicyclo-[9.3.1]pentadeca-1(15),11,13-triene-3,6,9-acetic acid |

TABLE 1-continued

Chelants used for complexation.

| Chelant | Name |
|---|---|
| (structure 5: cyclen with four CH2COOH arms) | 1,4,7,10-tetraazacyclododecane-1,4,7,10-tetraacetic acid (DOTA) |

For each example, the complexes were prepared by mixing 0.063 mL of an aqueous solution (20 mM) of chelant with $^{225}$Ac chloride solution (35 μL; 1 μCi/μL,) in 0.1M HCl. When complexation was performed at pH=6, the pH of the reaction mixture was set using 50% tetramethyl ammonium acetate (130 μL, 0.2 M, pH 6). When complexation was conducted at higher pH, the pH of the reaction mixture was set with 0.1 M sodium hydroxide. The final volume of the reaction mixture was 0.250 mL.

Complexation was carried out by incubating the reaction mixture at 20, 37 or 60° C. for 1, 3 or 24 hours. The chelant concentration was 5 mM. The degree of complexation was determined using cation exchange chromatography employing Sephadex C-25 resin.

Table 2 summarizer the reactions conditions and the results.

TABLE 2

Summary of the reaction conditions and results.

| Chelant | Temp (° C.) | pH | Time (h) | % complexation |
|---|---|---|---|---|
| 1 | 20 | 8 | 1 | 96.0 |
|  |  |  | 3 | 97.9 |
|  | 37 | 8 | 1 | 97.1 |
|  |  |  | 2 | 98.0 |
|  |  |  | 24 | 99.0 |
|  | 60 | 8 | 1 | 98.8 |
|  |  |  | 2 | 99.3 |
|  |  |  | 24 | 99.9 |
| 2 | 20 | 8 | 1 | 97.7 |
|  |  |  | 3 | 98.2 |
|  |  |  | 24 | 98.1 |
|  | 37 | 8 | 1 | 95.6 |
|  |  |  | 3 | 97.3 |
|  |  |  | 24 | 99.5 |
|  | 60 | 8 | 1 | 98.5 |
|  |  |  | 3 | 98.4 |
|  |  |  | 24 | 99.2 |

TABLE 2-continued

Summary of the reaction conditions and results.

| Chelant | Temp (° C.) | pH | Time (h) | % complexation |
|---|---|---|---|---|
| 3 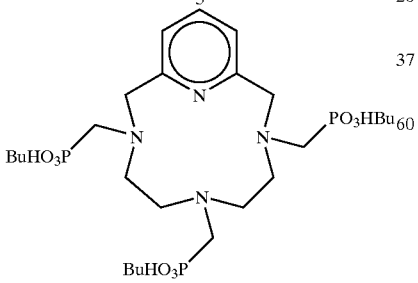 | 20 | 8 | 1 | 97.6 |
| | | | 3 | 95.1 |
| | | | 24 | 92.6 |
| | 37 | 8 | 1 | 93.6 |
| | | | 3 | 94.8 |
| | | | 24 | 90.1 |
| | 60 | 8 | 1 | 92.1 |
| | | | 3 | 88.5 |
| | | | 24 | 94.6 |
| 4 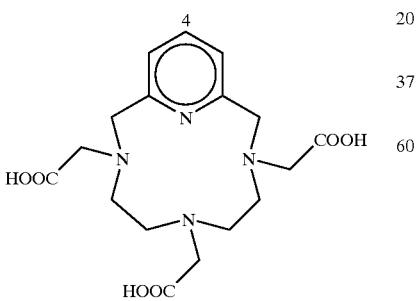 | 20 | 6 | 1 | 99.9 |
| | | | 3 | 100.0 |
| | | | 24 | 98.5 |
| | 37 | 6 | 1 | 99.9 |
| | | | 3 | 100.0 |
| | | | 24 | 99.3 |
| | 60 | 6 | 1 | 100.0 |
| | | | 3 | 100.0 |
| | | | 24 | 99.3 |
| 5 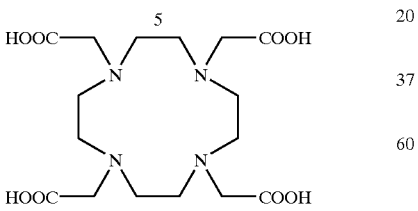 | 20 | 6 | 1 | 87.1 |
| | | | 3 | 95.0 |
| | | | 24 | 98.6 |
| | 37 | 6 | 1 | 99.2 |
| | | | 3 | 99.5 |
| | | | 24 | 99.1 |
| | 60 | 6 | 1 | 100.0 |
| | | | 3 | 99.9 |
| | | | 24 | 99.1 |

What is claimed is:

1. An Actinium-225 complex comprising a functionalized polyazamacrocyclic chelant compound of the formula I, hereinbelow:

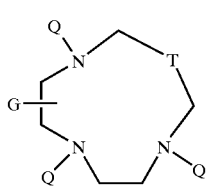

I wherein:

T is 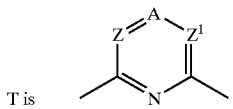

G is independently hydrogen or

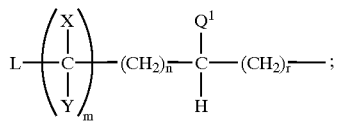

each Q is independently hydrogen, $(CHR^5)_pCO_2R$ or $(CHR^5)_pPO_3R^6R^7$ or

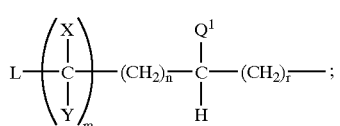

$Q^1$ is hydrogen, $(CHR^5)_wCO_2R$ or $(CHR^5)_wPO_3R^6R^7$;

each R is independently hydrogen, benzyl or $C_1$–$C_4$ alkyl;

$R^6$ and $R^7$ are independently H, $C_1$–$C_6$ alkyl or ($C_1$–$C_2$ alkyl) phenyl;

each $R^5$ is independently hydrogen; $C_1$–$C_4$ alkyl or ($C_1$–$C_2$ alkyl) phenyl;

with the proviso that at least two of the sum of Q and $Q^1$ must be other than hydrogen;

A is CH, N, C—Br, C—Cl, C—$SO_3H$, C—$OR^8$, C—$OR^9N^+$—$R^0X^-$, or

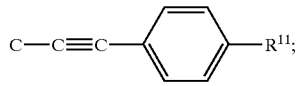

Z and $Z^1$ independently are CH, N, C—$SO_3H$, $N^+$—$R^{10}X^-$, C—$CH_2$—$OR^8$ or C—C(O)—$R^{11}$;

$R^8$ is H, $C_1$–$C_5$ alkyl, benzyl, or benzyl substituted with at least one $R^{12}$;

$R^9$ is $C_1$–$C_{16}$ alkylamino;

$R^{10}$ is $C_1$–$C_{16}$ alkyl, benzyl, or benzyl substituted with at least one $R^{12}$;

$R^{11}$ is —O—($C_1$–$C_3$ alkyl), OH or $NHR^{13}$;

$R^{12}$ is H, $NO_2$, $NH_2$, isothiocyanato, semicarbazido, thiosemicarbazido, maleimido, bromoacetamido or carboxyl;

$R^{13}$ is $C_1$–$C_5$ alkyl;

X and Y are each independently hydrogen or may be taken with an adjacent X and Y to form an additional carbon—carbon bond;

n is 0 or 1;

m is an integer from 0 to 10 inclusive;

p is 1 or 2;

r is 0 or 1;

w is 0 or 1;

with the proviso that n is only 1 when X and/or Y form an additional carbon—carbon bond, and the sum of r and w is 0 or 1;

L is a linker/spacer group covalently bonded to, and replaces one hydrogen atom of one of the carbon atoms to which it is joined, said linker/spacer group being represented by the formula

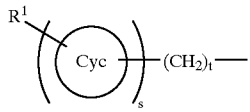

wherein:
s is an integer of 0 or 1;
t is an integer of 0 to 20 inclusive;
$R^1$ is H or an electrophilic or nucleophilic moiety which allows for covalent attachment to a biological carrier, or synthetic linker which can be attached to a biological carrier, or precursor thereof; and
Cyc represents a cyclic aliphatic moiety, aromatic moiety, aliphatic heterocyclic moiety, or aromatic heterocyclic moiety, each of said moieties optionally substituted with one or more groups which do not interfere with binding to a biological carrier;
with the proviso that when $R^1$ is H, the linkage to the biological carrier is through one of Q or $Q^1$; and with the proviso that when $R^1$ is other than H, at least one of Q and $Q^1$ must be $(CHR^5)_pPO_3R^6R^7$; and with further proviso that when Q is $(CHR^5)_pCO_2R$, $Q^1$ is $(CHR^5)_wCO_2R$, R is H, $R^5$ is H, and $R^1$ is H, then the sum of m, n, p, r, s, t, and w is greater than 1;

or pharmaceutically acceptable salt thereof; complexed with $^{225}$Ac.

2. A conjugate comprising the complex of claim 1 covalently attached to a biological carrier.

3. The conjugate according to claim 2 wherein the biological carrier is a protein, antibody, antibody fragment, hormone, peptide, growth factor, antigen or hapten.

4. The complex of claim 1 wherein $R^1$ is H, $NO_2$, $NH_2$, isothiocyanato, semicarbazido, thiosemicarbazido, maleimido, bromoacetamido or carboxyl.

5. An Actinium-225 complex comprising a functionalized polyazamacrocyclic chelant compound of formula IV, hereinbelow:

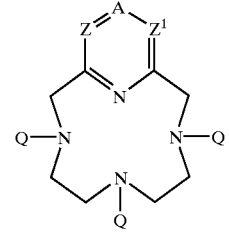

IV wherein:
each Q is independently hydrogen, $(CHR^5)_pCO_2R$ or $(CHR^5)_pPO_3R^6R^7$ or

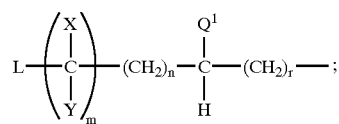

$Q^1$ is hydrogen, $(CHR^5)_wCO_2R$ or $(CHR^5)_wPO_3R^6R^7$;

each R is independently hydrogen, benzyl or $C_1$–$C_4$ alkyl;

$R^6$ and $R^7$ are independently H, $C_1$–$C_6$ alkyl or ($C_1$–$C_2$ alkyl) phenyl;

each $R^5$ is independently hydrogen; $C_1$–$C_4$ alkyl or ($C_1$–$C_2$ alkyl)phenyl;

with the proviso that at least two of the sum of Q and $Q^1$ must be other than hydrogen;

A is CH, N, C—Br, C—Cl, C—$SO_3H$, C—$OR^8$, C—$OR^9N^+$—$R^{10}X^-$, or

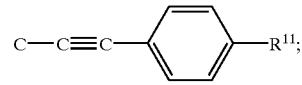

Z and $Z^1$ independently are CH, N, C—$SO_3H$, $N^+$—$R^{10}X^-$, C—$CH_2$—$OR^8$ or C—C(O)-$R^{11}$;

$R^8$ is H, $C_1$–$C_5$ alkyl, benzyl, or benzyl substituted with at least one $R^{12}$;

$R^9$ is $C_1$–$C_{16}$ alkylamino;

$R^{10}$ is $C_1$–$C_{16}$ alkyl, benzyl, or benzyl substituted with at least one $R^{12}$;

$R^{11}$ is —O—($C_1$–$C_3$ alkyl), OH or $NHR^{13}$;

$R^{12}$ is H, $NO_2$, $NH_2$, isothiocyanato, semicarbazido, thiosemicarbazido, maleimido, bromoacetamido or carboxyl;

$R^{13}$ is $C_1$–$C_5$ alkyl;

X and Y are each independently hydrogen or may be taken with an adjacent X and Y to form an additional carbon—carbon bond;

n is 0 or 1;

m is an integer from 0 to 10 inclusive;

p is 1 or 2;

r is 0 or 1;

w is 0 or 1;

with the proviso that n is only 1 when X and/or Y form an additional carbon—carbon bond, and the sum of r and w is 0 or 1;

L is a linker/spacer group covalently bonded to, and replaces one hydrogen atom of one of the carbon atoms to which it is joined, said linker/spacer group being represented by the formula

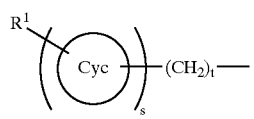

wherein:
s is an integer of 0 or 1;
t is an integer of 0 to 20 inclusive;
$R^1$ is H or an electrophilic or nucleophilic moiety which allows for covalent attachment to a biological carrier, or synthetic linker which can be attached to a biological carrier, or precursor thereof; and
Cyc represents a cyclic aliphatic moiety, aromatic moiety, aliphatic heterocyclic moiety, or aromatic heterocyclic moiety, each of said moieties optionally substituted with one or more groups which do not interfere with binding to a biological carrier;
with the proviso that when $R^1$ is H, the linkage to the biological carrier is through one of Q or $Q^1$; and with the proviso that when $R^1$ is other than H, at least one of Q and $Q^1$ must be $(CHR^5)_p PO_3 R^6 R^7$; and with further proviso that when Q is $(CHR^5)_p CO_2 R$, $Q^1$ is $(CHR^5)_w CO_2 R$, R is H, $R^5$ is H, and $R^1$ is H, then the sum of m, n, p, r, s, t, and w is greater than 1;

or a pharmaceutically acceptable salt thereof; complexed with $^{225}$Ac.

6. An Actinium-225 complex comprising a functionalized polyazamacrocyclic chelant compound of formula V, hereinbelow:

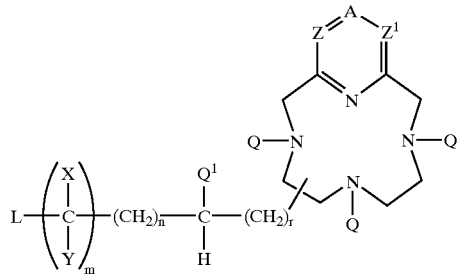

wherein:

each Q is independently hydrogen, $(CHR^5)_p CO_2 R$ or $(CHR^5)_p PO_3 R^6 R^7$ or

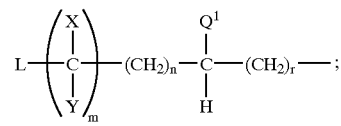

$Q^1$ is hydrogen, $(CHR^5)_w CO_2 R$ or $(CHR^5)_w PO_3 R^6 R^7$;

each R is independently hydrogen, benzyl or $C_1$–$C_4$ alkyl;

$R^6$ and $R^7$ are independently H, $C_1$–$C_6$ alkyl or ($C_1$–$C_2$ alkyl) phenyl;

each $R^5$ is independently hydrogen; $C_1$–$C_4$ alkyl or ($C_1$–$C_2$ alkyl) phenyl;

with the proviso that at least two of the sum of Q and $Q^1$ must be other than hydrogen;

A is CH, N, C—Br, C—Cl, C—$SO_3$H, C—$OR^8$, C—$OR^9 N^+$—$R^{10} X^-$, or

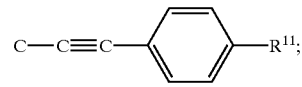

Z and $Z^1$ independently are CH, N, C—$SO_3$H, $N^+$—$R^{10} X^-$, C—$CH_2$—$OR^8$ or C—C(O)—$R^{11}$;

$R^8$ is H, $C_1$–$C_5$ alkyl, benzyl, or benzyl substituted with at least one $R^{12}$;

$R^9$ is $C_1$–$C_{16}$ alkylamino;

$R^{10}$ is $C_1$–$C_{16}$ alkyl, benzyl, or benzyl substituted with at least one $R^{12}$;

$R^{11}$ is —O—($C_1$–$C_3$ alkyl), OH or NHR⁻;

$R^{12}$ is H, $NO_2$, $NH_2$, isothiocyanato, semicarbazido, thiosemicarbazido, maleimido, bromoacetamido or carboxyl;

$R^{13}$ is $C_1$–$C_5$ alkyl;

X and Y are each independently hydrogen or may be taken with an adjacent X and Y to form an additional carbon—carbon bond;

n is 0 or 1;

m is an integer from 0 to 10 inclusive;

p is 1 or 2;

r is 0 or 1;

w is 0 or 1;

with the proviso that n is only 1 when X and/or Y form an additional carbon—carbon bond, and the sum of r and w is 0 or 1;

L is a linker/spacer group covalently bonded to, and replaces one hydrogen atom of one of the carbon atoms to which it is joined, said linker/spacer group being represented by the formula

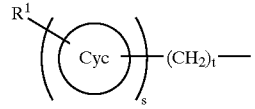

wherein:
s is an integer of 0 or 1;
t is an integer of 0 to 20 inclusive;
$R^1$ is H or an electrophilic or nucleophilic moiety which allows for covalent attachment to a biological carrier, or synthetic linker which can be attached to a biological carrier, or precursor thereof; and Cyc represents a cyclic aliphatic moiety, aromatic moiety, aliphatic heterocyclic moiety, or aromatic heterocyclic moiety, each of said moieties optionally substituted with one or more groups which do not interfere with binding to a biological carrier;

with the proviso that when $R^1$ is H, the linkage to the biological carrier is through one of Q or $Q^1$; and with the proviso that when $R^1$ is other than H, at least one of Q and $Q^1$ must be $(CHR^5)_p PO_3 R^6 R^7$; and with further proviso that when Q is $(CHR^5)_p CO_2 R$, $Q^1$ is $(CHR^5)_w CO_2 R$, R is H, $R^5$ is H, and $R^1$ is H, then the sum of m, n, p, r, s, t, and w is greater than 1;

or a pharmaceutically acceptable salt thereof; complexed with $^{225}Ac$.

7. A conjugate according to claim 2 comprising the $^{225}Ac$ complex of 3,9-carboxymethyl-6-(2-methoxy-5-isothiocyanatophenyl)carboxymethyl-3,6,9,15-tetraazabicyclo-[9.3.1]pentadeca-1(15),11,13-triene covalently attached to a biological carrier.

8. A pharmaceutical formulation comprising the $^{225}Ac$ conjugate of claim 2 and a pharmaceutically acceptable carrier.

9. The formulation of claim 8 wherein the pharmaceutically acceptable carrier is a liquid.

10. A method of therapeutic treatment of a mammal having cancer which comprises administering to said mammal a therapeutically effective amount of the formulation of claim 8.

* * * * *